United States Patent
Beiman et al.

(10) Patent No.: US 6,312,728 B1
(45) Date of Patent: *Nov. 6, 2001

(54) SUSTAINED RELEASE PHARMACEUTICAL PREPARATION

(75) Inventors: Elliott Beiman, Morristown; Fred Landsman, Princeton, both of NJ (US)

(73) Assignee: Cascade Development, Inc., Paradise Valley, NV (US)

(*) Notice: Subject to any disclaimer, the term of this patent is extended or adjusted under 35 U.S.C. 154(b) by 0 days.

This patent is subject to a terminal disclaimer.

(21) Appl. No.: 09/338,716

(22) Filed: Jun. 23, 1999

Related U.S. Application Data

(63) Continuation-in-part of application No. 09/111,188, filed on Jul. 7, 1998, now Pat. No. 5,968,554.

(51) Int. Cl.$^7$ .............................. A61K 9/36; A61K 9/24; A61K 9/32; A61K 9/16; A61K 9/22
(52) U.S. Cl. .................. 424/490; 424/472; 424/489; 424/480; 424/482; 424/494; 424/468; 424/458; 424/496; 424/497; 424/498; 424/481; 424/476; 424/495
(58) Field of Search ..................................... 424/468, 480, 424/2, 472, 476, 489, 490, 495, 6, 497, 8, 461, 462, 494, 481, 474, 458

(56) References Cited

U.S. PATENT DOCUMENTS

| | | | |
|---|---|---|---|
| 4,968,508 | 11/1990 | Oren et al. | 424/468 |
| 4,994,260 | 2/1991 | Källstrand et al. | 424/10 |
| 5,102,668 | 4/1992 | Eichel et al. | 424/490 |
| 5,188,836 | 2/1993 | Muhammad et al. | 424/431 |
| 5,229,131 | 7/1993 | Amidon et al. | 424/451 |
| 5,238,686 | 8/1993 | Eichel | 424/401 |
| 5,286,493 | 2/1994 | Oshlack et al. | 424/497 |
| 5,540,945 * | 7/1996 | Ikushima | 424/490 |
| 5,968,554 * | 10/1999 | Beiman et al. | 424/480 |

OTHER PUBLICATIONS

An article entitled: "Sustained Release of Phenytoin Following the Oral Administration of Phenytoin Sodum/Ethylcellulose Microcapsules in Human Subjects and Rabbits" authored by Karakasa et al. in *Biol. Pharm. Bull.*, 17(3) 432–436 (1994).

An article entitled: "Physiological and Pharmacokinetic Factors Affecting Performance of sustained Release Dosage Forms" authored by Boxenbaum in *Drug Development & Industrial Pharmacy*, 1982, 8(v), 1–25.

An article entitled: "Pharmacokinetic Evaluation of Sustained Release Formulations of Antiepileptic Drugs . . . Clinical Implications" authored by Bialer et al. in *Clinical Pharmacokinetics*, 22(1), 11–21, 1992.

An article entitled: "Computer–Aided Dosage Form Design. III. Feasibility Assessment for an Oral Prolonged–Release Phenytoin Product" authored by Irvin et al in *Pharmaceutical Research*, vol. 8, No. 2, 1991.

An article entitled: "Microencapsulation of Drugs by Pan and Air Suspension Techniques" authored by Deasy in *Critical Reviews in Therapeutic Drug Carrier Systems*, 8(1):39–89 (1991).

A paper entitled: "Important Pharmacokinetic Properties of Antiepileptic Drugs" authored by Bourgeois in *Epilepsia*, vol. 36 (Supp. 5) 1995.

An article entitled: "Absorption characteristics of three phenytoin sodium products after administration of oral loading doses" published in *Clinical Pharmacy*, vol. 3, Nov.–Dec. 1984 authored by Goff et al.

An article entitled: "Phenytoin Sodium Microcapsules: Bench Scale Formulation, Process Characterization and Release Kinetics" authored by Yazici et al. in *Pharmaceutical Development and Technology*, 1(2), 175–183 (1996).

* cited by examiner

*Primary Examiner*—James M. Spear
*Assistant Examiner*—Blessing Fubara
(74) *Attorney, Agent, or Firm*—Donald O. Nickey; Michael D. Steffensmeier

(57) ABSTRACT

The present invention pertains to a sustained release drug delivery system which comprises a core of active ingredient, an enteric coating, a second coating of active ingredient and lastly a readily gastric-soluble protective coating. In another embodiment, the sustained release drug delivery system comprises a core of active ingredient, an enteric coating; a second coating of active ingredient; a second enteric coating and a third coating of active ingredient The sustained release dosage form of this invention is useful for pharmaceutically active ingredients that have limited aqueous solubility, especially phenytoin sodium, and other pH dependent soluble drugs.

32 Claims, No Drawings

SUSTAINED RELEASE PHARMACEUTICAL PREPARATION

CROSS REFERENCE TO RELATED APPLICATIONS

This application is a continuation-in-part of U.S. patent application Ser. No. 09/111,188, filed Jul. 7, 1998, by Beiman, et al., now U.S. Pat. No. 5,968,554.

FIELD OF THE INVENTION

This invention relates to sustained release pharmaceutical preparations and to a method for making them. The novel drug delivery system contains a core comprising the active pharmaceutical, an enteral coating over the core comprising a pH dependent water soluble polymer, a second coating of the active pharmaceutical, and thereafter a coating which is soluble in gastric juices. The invention, in another embodiment, comprises a core of active, an enteral coating over the core comprising a pH dependent soluble polymer that breaks down in the colon and/or large intestine, a second coating of active, a second enteral coating that dissolves primarily in the small intestine, a third layer of active and, a protective coating that is soluble in gastric juices. The drug delivery system of the invention may be utilized with a wide variety of pharmaceutically active agents which have pH dependent solubilities to prepare sustained release compositions. This invention also relates to a novel method for preparing these drug delivery systems and to sustained release compositions made thereby.

BACKGROUND OF THE INVENTION

A sustained release dosage form may be defined as a preparation which releases a drug, in vivo, at a considerably slower rate than is the case from an equivalent dose of a conventional (non-sustained release) dosage form. The objective of employing a sustained release product is to obtain a satisfactory drug response while at the same time, reducing the frequency of administration. An example of a drug which is popularly used in a sustained release form is chlorpheniramine maleate. In conventional form, the drug may be given as 4 mg doses every four (4) hours or in sustained release form as 12 mg every twelve (12) hours.

Sustained release compositions for the sequential or timed release of medicaments are well known in the art. Generally, such compositions contain medicament particles, normally administered in divided doses two (2) or three (3) times daily, mixed with or covered by a coating material which is resistant to degradation or disintegration in the stomach and/or in the intestine for a selected period of time. Release of the medicament may occur by leeching, erosion, rupture, diffusion or similar actions depending upon the nature and thickness of the coating material.

It is known that different pharmaceutical preparations of the same active ingredient will result in different bioavailabilities of the active ingredient to the mammal. Bioavailability or biological availability may be defined as the percentage of the drug liberated from the dosage form administered that becomes available in the body for biological effect. Different formulations of the same drug can vary in bioavailability to a clinically relevant extent and variation may even occur between batches of the same product due to subtle variations in manufacturing procedures.

Many drugs that are usually administered in tablet or capsule form have a low solubility in biological fluids. For many drugs of low solubility, there is considerable evidence that the dissolution rate, partially or completely controls the rate of absorption. Bioavailability can also be affected by a number of factors such as the amounts and types of adjuvants used, the granulation process, compression forces (in tablet manufacturing), surface area available for dissolution and environmental factors such as agitation in the stomach and the presence of food. Due to these numerous factors, specific formulations play an important role in the preparation of prolonged action solid dosage forms.

Epilepsy is an ancient disease which affects about 1% of the global population. Despite the progress made in antiepileptic drug therapy, there are still many patients who continue to suffer from uncontrolled seizures and medication toxicity. At present, only four (4) major antiepileptic drugs are in use: phenobarbital, phenytoin sodium, carbamazepine and valporic acid.

Pharmacological activity, in general, and antiepileptic activity in particular, correlate better with a concentration of the drug in the blood (or in some other biophase) than with the administered dose. This phenomenon is due, in part, to variability in drug absorption and disposition between and within individuals, particularly when the drug is given orally. Optimizing drug therapy aims at achieving and maintaining therapeutic and safe drug concentrations in the patient's plasma. It would thus be advantageous that the patient receive a once- or twice-daily dosage regimen.

Phenytoin is 5,5-diphenyl-2,4-imidazolidinedione. It is a well-known pharmaceutical agent having anti-convulsant and antiepileptic activity. Due to phenytoin's poor solubility in water, phenytoin sodium, of empirical formula $C_{15}H_{11}N_2NaO_2$, which is much more soluble, is employed in the preparation of injectable solutions of the drug and in solid enteral dosage forms.

While phenytoin is the antiepileptic drug of choice for most types of epileptic seizures, except for petit mal, therapeutic drug monitoring is required because of the difficulty in maintaining an effective therapeutic plasma level of between 10 and 20 $\mu g/ml$. In addition to the problems of narrow therapeutic plasma levels, phenytoin has exhibited great variations in bioavailability following its oral administration to patients because of its poor water solubility.

With even the new approaches to phenytoin delivery (i.e., Parke-Davis' Dilantin® Kapseals®, which are 100 mg extended phenytoin sodium capsules), it is still necessary for patients to take the drug several times a day to maintain an effective therapeutic plasma level without side effects. While many encapsulation techniques have been attempted, none have been found to be satisfactory. Karakasa et al., *Biol. Pharm. Bull.*, 17(3) 432–436 (1994) in an article entitled "Sustained Release of Phenytoin Following) the Oral Administration of Phenytoin Sodium/Ethylcellulose Microcapsules in Human Subjects and Rabbits", studied the release patterns of phenytoin as the sodium salt in combination with ethylcellulose. The phenytoin sodium microcapsules were prepared by mixing 80 weight % of the phenytoin sodium in a 10% (w/v) ethylcellulose solution in ethylacetate. The suspension was stirred and n-pentane was added dropwise until a phase separation occurred and the microcapsules were obtained. The microcapsules were collected on filter paper, dried and stored. Karakasa et al. point out that following the oral administration of phenytoin sodium, the salt might be easily transferred into free-phenytoin in the acidic fluids of the stomach. As free-phenytoin is practically insoluble in water, its absorption might be incomplete in the gastrointestinal tract. On the other hand, while passing through the stomach, the volume of water penetrating into the ethylcellulose microcapsules might be minimal. Thus, most of the phenytoin sodium in the microcapsules might not be converted into free-phenytoin. This reference fails to suggest a dosage form wherein a portion of the active ingredient is released in the stomach and the remaining portion is released in the intestines.

A review article by Boxenbaum in *Drug Development & Industrial Pharmacy*, 1982, 8(v), 1–25, entitled "Physiological and Pharmacokinetic Factors Affecting Performance of Sustained Release Dosage Forms" actually suggests that sustained release formulations for drugs such as phenytoin are unnecessary. Boxenbaum points out that dosing schedules of once a day versus three times daily produce similar plasma curves. This results from both the slow absorption, disposition of the drug and the low solubility.

It is the inventor's position that slow release, delayed release, prolonged release or sustained release phenytoin is a desirable objective. Controlled release oral dosage forms of drugs with long half lives, such as phenytoin, have been previously disregarded for sustained release formulation since they produce little chance in the blood concentration after multiple doses have been administered. The existence of such products can, however, be justified, on the basis of their ability to minimize toxicity and the occurrence of adverse reactions and as providing greater patient convenience and thus, better patient compliance.

Bialer in an article entitled, "Pharmacokinetic Evaluation of Sustained Release Formulations of Antiepileptic Drugs . . . Clinical Implications" in *Clinical Pharmacokinetics* 22(1): 11–21 1992, also suggests that phenytoin is not a suitable candidate for sustained release formulations. What Bialer and Boxenbaum have failed to realize is that through the novel use of the physical properties of phenytoin sodium and drugs like phenytoin sodium , one can prepare a sustained release formulation that is beneficial to the patient.

The dosage form according to this invention has an essentially unprotected layer of active ingredient that is immediately released into the gastric juices of the stomach and a second, and optionally a third layer of active ingredient that is protected by an enteric coating. The second portion of the dose is made available subsequent to passage into the duodenum. The third portion is made available subsequent to passage into the large intestine, more preferably, the colon. The drug delivery system according to the present invention provides an unusually stable drug concentration profile in the plasma. Further, patients will benefit from such a formulation since many drugs like phenytoin have narrow therapeutic windows which require multiple (3 or more) daily dosings.

Further, Irvin et al., in an article in *Pharmaceutical Research*, Vol. 8, No. 2, 1991, entitled "Computer-Aided Dosage Form Design. III. Feasibility Assessment for an Oral Prolonged-Release Phenytoin Product" have also emphasized that phenytoin is not an acceptable candidate for prolonged release dosage forms. They go on to note that dosage forms which traverse the stomach tend to be expelled before the release of the phenytoin is complete. These teachings again fail to realize that a novel dosage form, having protected and unprotected components, can be effectively used to prepare a sustained release formula for drugs with pH dependent solubilities.

Deasy, *Critical Reviews in Therapeutic Drug Carrier Systems*, 8(1): 39–89 (1991) in an article entitled "Microencapsulation of Drugs by Pan and Air Suspension Techniques" states that drugs such as phenytoin with half-lives greater than six (6) hours, tend to have inherent sustained release properties and benefit little from prolonged released preparations. The Deasy article goes on to comment that drugs such as phenytoin, with narrow ranges of therapeutic plasma levels, present special problems when being formulated as sustained release preparations. This reference also provides a good general discussion of microencapsulation dosage forms prepared by the pan and air suspension methodologies.

A paper by Bourgcois entitled "Important Pharmacokinetic Properties of Antiepileptic Drugs" in *Epilepsia*, Vol. 36 (Supp. 5) 1995, discusses the important pharmacokinetic properties of antiepileptic drugs. The author states that a drug's rate of absorption profile is described by its absorption constant ($k_{abs}$). A high absorption constant results in early and high peak serum concentrations. A high ($kabs$) value also results in greater fluctuations in drug levels compared with the steadier concentrations resulting from lower ($kabs$) values. A lower absorption constant can often be produced by formulating an otherwise rapidly absorbed drug in a slow release preparation. However, enteric coated preparations do not alter a drug's ($k_{abs}$) value; they merely delay absorption. Enteric coating is designed to prevent absorption in the acidic environment of the stomach. Consider for example, a patient who has received a single dose of enteric coated valproate. For the first few hours after dosing, serum measurements will fail to detect any drug in the blood. Not until the tablet reaches the alkaline environment of the duodenum does the serum concentration rapidly increase, ultimately achieving a profile similar to that of an uncoated preparation of valproate. Therefore, the enterie coating merely shifts the time concentration profile to the right.

In a publication in *Clinical Pharmacy, Vol.* 3, November-December 1984, entitled "Absorption characteristics of three phenytoin sodium products after administration of oral loading doses" by Goff et al., the absorption characteristics of three (3) phenytoin sodium products after administration of oral loading doses is evaluated. Goff et al. suggest that the administration of intravenous phenytoin has been associated with serious adverse effects, including cardiac arrhythmias and hypotensioni. The reported study was conducted to deternine the effect of different phenytoin sodium preparations on the rate and extent of absorption following the administration of oral phenytoin loading doses. Goff et al. report that the absorption following oral administration of the phenytoin sodium solution was found to be erratic and highly variable among subjects. In the acid medium of the stomach, phenytoin sodium is rapidly changed to phenytoin acid with subsequent precipitation. The authors of this reference suggest that following the administration of the phenytoin sodium solution, the solubilizing agents were rapidly absorbed from the stomach and this could have resulted in the precipitation of the poorly soluble phenytoin acid in the stomach. A similar mechanism was proposed for the poor absorption of phenytoin following intra-muscular administration.

In an article by Yazici et al., entitled "Phenytoin Sodium microcapsules: Bench Scale Formula, Process Characterization and Release Kinetics" in *Pharmaceutical Development and Technology*, 1(2), 175–183 (1996), the preparation of phenytoin sodium microcapsules using ethylcellulose and methyl acrylic acid copolymers (Eudragit® S-100 and L-100) as coating materials is reported. The phenytoin sodium microcapsules were formulated by an organic phase separation and granule coating method. The optimum phenytoin sodium-to-ethylcellulose ratio of 1:2.3 was reported. The authors report that phenytoin sodium is a problem material as far as drug absorption is concerned as the rate determining step of phenytoin absorption is its release from dosage forms. The optimized experimental dosage forms were evaluated against sustained-action, commercially available capsules and found to give superimposable release characteristics. The authors fail to suggest that the dose of phenytoin sodium, in microcapsular form, be divided between enteric coatings. Neither the microcapsules nor the Yazici et al. method of production are at all similar to the presently claimed dosage form wherein the core comprises 25–75% of an effective amount of a therapeutic agent and one or two enteric coatings separating one or two additional layers of therapeutic agent (second and third portions), and finally a coating of a low pH soluble protective coating.

U.S. Pat. No. 4,968,508 to Oren et al. relates to a matrix composition for sustained drug delivery which is comprised of an active agent, a hydrophilic polymer and an enteric polymer. The enteric polymer is impermeable to gastric fluids and aids in retarding drug release in regions of low pH, thus allowing lower levels of hydrophilic polymer to be employed. Oren et al. suggest that this approach is useful in sustaining the release of numerous active agents whose solubility declines as the pH is increased, a characteristic of weekly basic drugs. The Oren et al. sustained release matrix was prepared using conventional hydrogel technology. This patent does not suggest nor disclose the division of a given dose of active agent by one or more enteric coatings. The enteric coating release a portion of the active after entry into the duodenum and a portion after entry into the large intestine.

U.S. Pat. No. 4,994,260 to Källstrand et al. relates to a pharmaceutical preparation for controlled release of a pharmaceutically active substance prepared by mixing, in an aqueous carrier, a pharmaceutically active substance encapsulated in a coating and 60–99% by weight of a release controlling substance selected from the group consisting of polysaccharides, oligosaccharides, disaccharides, monosaccharides, polyhydroxyalchohols and mixtures thereof. This patent describes the use of Eudragit® E 100 and sucrose to make the dosage form. The Eudragit® E 100 is a polymer soluble in acid.

U.S. Pat. No. 5,188,836 to Muhammad et al. discloses a semi-enteric, sustained release pharmaceutical consisting of a biologically active composition layered on an inert core and an outer inert coating consisting of a water insoluble methaciylic acid polymer, a water soluble sugar alcohol, a food grade acid and a plasticizer characterized by a two-tiered solubility profile in the human digestive tract. The dosage forms of this reference initially dissolve in the stomach and thereafter completely dissolves and is absorbed in the intestine. This patent discloses the use of Eudragit® L30D as a major coating constituent. In this reference, the release characteristics of Eudragit® L30D polymer are modified so that a semi-enteric formulation is created. The dissolution characteristics of Eudragit® L30D are modified through the inclusion of a water soluble bulking agent such as a sugar alcohol.

U.S. Pat. No. 5,102,668 to Eichel et al. discloses a pharmaceutical preparation that contains multiple units of microparticles comprising a granular drug that is less soluble at low pH and more soluble at high pH. The granular drug is admixed with or surrounded by a pH controlled material which is formed from at least one polymer that is hydrophilic at low pH and hydrophobic at higher pH. The pH controlled material is in a ratio with the granular drug such that the resulting sustained release pharmaceutical preparation is independent of the pH environment. Eudragit® E 100 is disclosed as a polymer which is useful in the invention since it is pH controlled.

U.S. Pat. No. 5,229,131 to Amidon et al. discloses a drug delivery system for administering a drug in controlled pulse doses in a aqueous environment over a predetermined dosage period of time. A unitary body contains a plurality of subunits. Each of the subunits has a core portion which contains an individual dose of the drug. The core is surrounded by a respectively associated coating portion which is formed of selected first and second polymer materials. The water permeable polymers are disclosed as including cellulose acetate, Eudragit® RS and Eudragit® R30D. The drug delivery system of the '131 patent is disclosed as being useful with beta-adrenergic blockers and antiepileptic drugs such as phenytoin.

U.S. Pat. No. 5,238,686 to Eichel et al. discloses a dual walled coated medicament having a water soluble core drug, an inner wall microencapsular coating and an outer wall enteric coating. By enterically coating the microcapsules, the release of core drug into the stomach is greatly impeded and the delivery of the drug is substantially delayed until the coated microcapsules reach the intestine. The dual walled medicament of the '686 patent is claimed to release less than 10% per hour of said drug while in the stomach, but will slowly release said drug in the intestines to provide adequate levels for eight (8) or more hours without resulting in excessively high drug levels at any time.

From a review of the prior art, it is quite evident that a need still remains for a sustained release system for drugs with pH dependent solubilities, such as phenytoin sodium, which provide initial therapeutic levels of the drug, delays the delivery of another fraction of the drug to eliminate excess concentrations for about 1–5 hours and then, sustains the release of that delayed fraction to provide adequate blood plasma drug levels for 12 or more hours.

SUMMARY OF THE INVENTION

The present invention meets the unfulfilled needs of the pharmaceutical industry by providing a medicament that has a given proportion of a required dose separated by enteric coatings. In another embodiment of the invention, the required dose of the therapeutic agent is separated by two (2) enteric coatings, the second coating providing release of the active after passage into the small intestines and the first enteric coating (closest to the core) providing release after passage into the large intestine and colon. The microcapsules according to the invention immediately release a portion of the drug into the stomach while allowing a portion of the drug to pass into the duodenum wherein the enteric coating dissolves and the drug is thereby slowly absorbed by the intestines. The unprotected portion of the microcapsule rapidly dissolves in the stomach and that portion of the drug dose quickly enters the bloodstream. The enterically coated portion of the drug begins to dissolve in the small intestine where a substantial increase in pH occurs to then controllably release the remainder of the active. In the two (2) enteric coating dosage form embodiment, the first dose is delivered in the stomach, as described above, the second dose in the small intestines and the third in the large intestine or colon. This is possible due to the presence of the extra layer of enteric coating. In the small intestines, the enteric coating or membrane dissolves or disperses in the intestinal fluid. In similar fashion, the enteric coating dissolves or disperses in the fluids of the large intestine and the colon. Depending upon the relatively pH solubility of the active agent, the percentage of total active inside or outside of the enteric coatings can be adjusted so that excess plasma drug concentrations are minimized and steady long-term release of the drug is maximized.

Thus, there is disclosed an oral dosage delivery form adapted to deliver a pH dependent water soluble therapeutic agent comprising:

(a) a core comprising said therapeutic agent in an amount sufficient to deliver a first portion of an effective amount of said therapeutic agent over the intended delivery time;

(b) an enteric polymer coating over said core;

(c) a coating of said therapeutic agent over said enteric polymer coating in an amount sufficient to deliver a second portion of an effective amount of said therapeutic agent over the intended delivery time; and (d) a low pH soluble protective coating over said coating of said therapeutic agent.

The first and second portions of the therapeutic agent can each range from 25 to 75% of the effective amount of the therapeutic agent. Thus, if the first portion is 25%, the second portion would be 75%.

In an alternative embodiment, the inventive oral dosage delivery form may omit the low pH soluble protective coating. The protective coating does not impact upon long-term release properties of the invention and is principally used to reduce or eliminate damage to the outer coating of the therapeutic agent. In yet another embodiment, the inventive oral delivery form additionally comprises an edible acid in the enteric polymer coating. It has been determined that inclusion of from about 5 to about 40% by weight of an edible acid, such as fumaric acid, in the enteric coating will make the coating resistant to dissolution in the relative alkaline environment of the small intestine. The inclusion of an acid in the enteric coating will further delay the release of drugs with pH dependent solubilities, thus making the inventive dosage form capable of 24-hour time release.

In yet another embodiment, there is disclosed an oral dosage delivery form adapted to deliver a pH dependent water soluble therapeutic agent comprising:

a) a core comprising said therapeutic agent in an amount sufficient to deliver a first portion of an effective amount of said therapeutic agent over the intended delivery time;

b) a first enteric polymer coating over said core;

c) a second layer of said therapeutic agent in an amount sufficient to deliver a second portion of an effective amount of said therapeutic agent over the intended delivery time;

d) a second enteric polymer coating over said second layer of therapeutic agent; and e) a third layer of said therapeutic agent over said second enteric polymer coating in an amount sufficient to delivery a third portion of an effective amount of said therapeutic agent over the intended delivery time.

The first, second and third portions of the therapeutic agent can each independently range from 25 to 75% of the effective amount of the therapeutic agent over the intended delivery time. Thus, for example, the core (first portion) may contain 25% of the dose for delivery to the large intestine/colon, the second portion may contain 50% for delivery to the small intestine and the third portion may contain 25% for delivery in the stomach.

The core is typically formed around a biologically inert sphere such as a non-pareil. A non-pareil, as known to those skilled in the art, is a sugar particle that is widely used in the pharmaceutical industry. The core of the therapeutically active agent may also contain other ingredients such as adhesives, anti-tack agents, disintegrants, antifoaming agents and lubricants. Especially preferred for use with phenytoin sodium is sodium lauryl sulfate. The presence of the sodium lauryl sulfate, enhances the solubility of this compound. This is especially true in the gastric fluids. The enteric polymer coating solution may also contain components such as plasticizers and anti-tack agents.

The final protective coating should be a material that rapidly dissolves or disperses in the gastric juices. This is required so as to accomplish the administration of from 25–75% of the dose in the stomach.

Thus, there is more specifically disclosed an oral dosage delivery form comprising:

(a) a core comprising phenytoin sodium, sodium lauryl sulfate and a disintegrant, said core containing 25–75% by weight of an effective amount of said phenytoin sodium over the intended delivery time;

(b) an enteric coating over said core, said enteric coating comprising an ethylacrylate methacrylic acid copolymer and a plasticizer;

(c) a coating over said enteric coating comprising phenytoin sodium, sodium lauryl sulfate and a disintegrant, said coating containing 25–75% by weight of an effective amount of said phenytoin sodium over the intended delivery time; and (d) a low pH soluble protective coating over said coating comprising phenytoin sodium.

The present invention also relates to a novel process for the preparation of a sustained release pharmaceutical dosage form. The method of the invention comprises the steps of:

(a) preparing an aqueous suspension of a therapeutic agent wherein said agent's solubility is pH dependent;

(b) preparing an enteric coating aqueous solution comprising a material that does not dissolve or disperse in gastric juices;

(c) charging an air suspension coating machine with biologically inert spherical pellets;

(d) spraying 25–75 weight % of said suspension of therapeutic agent while said air suspension coating machine is in operation to coat said inert pellets; thereafter (e) spraying said enteric coating aqueous solution to coat the pellets of step (d); and thereafter, optionally, (f) spraying the remainder of said suspension of therapeutic agent to coat the pellets of step (e).

It is the inventors' work in the field of preparing medicaments through the use of fluidized bed or air suspension coating machines that led to the discoveries resulting in the inventive oral dosage forms and methods for their production. As the dosage form itself is ultimately tied to its method of production, claims directed to the dosage form itself and its method of production are appropriate.

As mentioned previously, the core of the inventive delivery form may be formed around an inert seed, such as non-pareils, with a 10 to 100 mesh. The core may also contain a disintegrant and processing aids. As used herein and in the claims, the phrase "enteric polymer coating" means any coating that does not dissolve in the acidic environment of the stomach, but does dissolve at a pH of 5.0 or higher. Representative enteric polymer coatings may be selected from the group consisting of ethylcellulose, hydroxypropylcellulose and carboxymethylcellulose. Ethylcellulose is a common, microencapsular coating which will not readily dissolve or disperse in the stomach. Other aqueous or solvent based enteric coatings may be used as long as they do not readily dissolve or disperse in the gastric juices of the stomach but do dissolve or disperse in the intestinal fluid. Blends of various enteric polymers may also be used. For example, acrylic resins, shellac, wax or other film forming materials which will dissolve or disperse in the intestine but remain intact in the stomach, are possible alternatives. Most preferably, the enteric polymer coating comprises a water based emulsion polymer. A useful enteric coating is an ethylacrylate methacrylic acid copolymer sold under the trademark Eudragit® by Rhom GmbH of Domstadt, Germany. A preferred enteric polymer coating is Eudragit® L30D which has a molecular weight of about 250,000 and is generally applied as a 25–75% aqueous solution. The most preferred enteric coating is Eudragit® L30D-55 and is applied as a 45–55 weight % aqueous solution. Other Eudragits® such as HP50, HP55 and L100 would also be useful.

In the embodiment of the present invention, where there are two (2) coatings of enteric polymer separating three (3) doses of active, the first coating (closest to the core) is preferably an enteric coating that will survive until the dosage form arrives at the large intestine/colon. A preferred enteric coating is a series of methacrylic acid anionic copolymers known as Eudragit®S, manufactured by Röhm Pharma GmbH of Darmstadt, Germany. The Eudragit S films are colorless, transparent and brittle. They are insoluble in pure water, in buffer solutions below a pH of 6.0 and also in natural and artificial gastric juices. They are slowly soluble in the region of the digestive tract where the juices are neutral to weakly alkaline (i.e., the large intestine and the colon) and in buffer solutions above a pH of 7.0. Mixtures of these various enteric polymers recited above, can be used in the present invention. Further, the use of plasticizers is preferred in the enteric polymer coatings useful herein.

The enteric coating may also be modified through the inclusion of an edible acid to retard or slow the dissolution of the coating in the intestines. Any edible acid may be used. Representative edible acids include acetic acid, benzoic acid, fumaric acid, sorbic acid, propionic acid, hydrochloric acid, citric acid, malic acid, tartaric acid, isocitric acid, oxalic acid, lactic acid, the phosphoric acids and mixtures thereof. Especially preferred is fumaric acid and malic acids. The weight percent of the edible acid in the enteric coating solution (polymer, plasticizer, anti-tack agents, water and the like) can range from about 5 to about 40%, with 10 to 30% being more preferred and 10 to 25% being most preferred. Those skilled in the art will readily be able to determine the exact amount of edible acid to include in the coating solution, depending upon the pKa of the particular edible acid and the desired delay in dissolution of the enteric coating. After application of the enteric coating solution, as further described below, the percent of edible acid in the coating will range from about 10 to about 80 weight % of the coating; more preferably 20 to 60%; and most preferably 25–50%.

The coating of the therapeutic agent over the enteric coating may be identical to the composition of the core, except for the inert seed, or it may vary to some extent. The therapeutic agent itself will remain the same, however, the disintegrate(s), lubricant(s), tackifying agent(s), partitioning agent(s), processing aid(s) and the like may vary.

The low pH soluble protective coating may be any material that readily dissolves in the stomach fluids (pH of about 1.5 to 3.0) and provides protection to the underlying coating of the therapeutic agent. At least, the protective coating will prevent abrasion to the coating of the therapeutic agent, reduce water absorption and reduce adhesion between individual dosage forms. Representative of useful materials for the protective coating include Methocel® and other cellulosics and sugars that are water soluble. As mentioned previously, the low pH soluble protective coating may be omitted from the inventive dosage form, however, the preferred dosage form does include the protective coating.

One aspect of the present invention relates to the discovery that pH dependent water soluble therapeutic agents, such as phenytoin sodium, can be placed in the dosage delivery form according to this invention, to yield sustained blood plasma concentrations of the therapeutic agent. More specifically, the present invention provides that from 25 to 75% of the therapeutic agent be present in the core of the dosage delivery form and that the remainder of the therapeutic agent be present in the coating over the enteral polymer coating or divided between the second and third layers of the therapeutic agent. It has been discovered that for therapeutic agents which have solubilities that vary according to the pH, the present invention is effective in overcoming variable blood plasma concentrations that these therapeutic agents typically exhibit. More specifically, for phenytoin sodium, it has been discovered that about 50% by weight of a given dose should be in the core and about 50% should be in the coating over the enteric polymer coating. Most preferably, the core contains about 48% by weight of the phenytoin sodium and about 52% by weight of the phenytoin sodium should be in the coating over the enteric coating. It will be understood by the skilled artisan that the effective amounts are over an intended delivery time and for a desired blood plasma concentration.

The pharmaceutically active compounds that will benefit from the dosage form according to the invention include the typical salts of organic nitrogenous compounds such as the chlorides, fluorides, malcates, succinates, tartates, carbamates, acetates, sulfates, phosphates, lactates, citrates and the like. The alkali metal and alkaline earth metal salts of organic nitrogenous compounds which have pH dependent solubilities will also benefit from the oral dosage form of this invention. These representative salts of pharmaceutically active compounds experience a shift in water solubility as the pH of the environment in which it resides (i.e., stomach versus intestinal tract) changes.

Those skilled in the art will appreciate that following oral administration of a drug, the dissolution rate is of primary importance in determining eventual levels attained in the blood and tissues. If the drug is too insoluble in the environment of the gastrointestinal tract to dissolve at an appreciable rate, it cannot diffuse to the gastrointestinal wall and be absorbed. These are factors that relate to the "prolonged action" of the dosage form.

In part, the present invention takes advantage of the major variations in acidity in the animal body for various body compartments; the high acidity (about pH 1) of the stomach, the relatively neutral environment of the lumen (about 6.6); the plasma (about 7.4); the large intestine and the colon (about 7.0); and most body tissues and organs (cerebrospinal fluid, pH 7.4).

Most drugs are weak acids or bases, and the degree of their ionization, as determined by the dissociation constant (pKa) of the drug and pH of the environment, influences their solubilities. The dissociation constant (pKa) is the negative log of the acidic dissociation constant and is the preferred expression for both acids and bases. An acid with a small pKa (i.e., about 1.0) placed in an environment with a pH of 7 would be almost completely ionized and would be classified as a strong acid. In contrast, when a weak base passes from the strongly acidic environment of the stomach into the less acidic intestinal lumen, the extent of ionization decreases. The concentration of un-ionized species for a base with a pKa of about 4.0 is about 10 times that of the ionized species and since the neutral molecule freely diffuses through the intestinal mucosa, the drug is well absorbed.

The split of the active agent outside or inside the enteric coating, in part, can be co-related to the reduction in the extent of absorption from the intestine for acids with a pKa of less than about 2.5 and for bases with a pKa of greater than about 8.5. With these and other factors in mind, a dosage form in accordance with the present invention can be prepared that accomplishes relatively consistent levels of the active in the blood serum. Thus, representative pharmaceutically active salts that will benefit from the dosage form of the present invention include: diphendyramine hydrochloride (Benadiyl®), dimenhydrinate (Dramaminie®), bromodiphenhydramine hydrochloride (Ambodryl®), doxylamine succinate (Decapryn® succinate), phenyltoloxamine dihydrogen citrate (Bristamin®), carbinoxyamine maleate (Clistin®), chlorpheniraminie maleate, promethazine hydrochloride (Phenergan®), cyclizine hydrochloride (Marezine®), diltiazam hydrochloride (Cardizem®), disopyramide phosphate (Norpace®), iodihippurate sodium (Hippuran®), phenylpropanolamine hydrochloride, propranolol hydrochloride (Inderal®), thiopeental sodium, mephenesin carbamate, hydroxyzine hydrochloride, benactyzine hydrochloride, methamphetamine hydrochloride, phenylpropanol-amine hydrochloride, ephdrine sulfate and iproniazid phosphate.

While there are many and varied active agents that may beneficially utilize the dosage form of the present invention, it is important to consider each active agent's reaction to the gastric and intestinal environments. These considerations will dictate the actual manufacturing procedure.

The division of the given dosage between the enteric coatings can be controlled through the manufacturing process. Those skilled in the art will be able to adjust the air suspension of a fluidized bed, a rotor (rotating disc), or a Wurster column device to accomplish the desired result. Spray rates through appropriate nozzles are also known to those proficient in the trade.

The invention will be better understood from the following Examples which are only representative of the invention as set forth in the claims.

EXAMPLE I

Preparation of Beads According, to the Invention

Using conventional equipment and techniques, the following compositions were prepared:

| Ingredient | Amount (Kg) |
|---|---|
| Therapeutic Suspension | |
| Active - Phenytoin Sodium, USP | 3.2 |
| Adhesive - HPMC, E-5 LV (Methocel) | 0.558 |
| Anti-tack - Talc, USP | 0.558 |
| Disintegrant - Cross carmellose Sodium | 0.117 |

| Ingredient | Amount (Kg) |
|---|---|
| Antifoam - Silicon Medical Antifoam emulsion | 0.027 |
| Lubricant - Magnesium Stearate | 0.225 |
| Solvent - Water | 9.5 |
| Na lauryl sulfate | 0.140 |
| TOTAL | 14.325 |
| Enteric Coating | |
| Polymer - Eudragit L30D-55 | 3.0 |
| Plasticizer - Triethyl citrate | 0.09 |
| Anti-Tack - Talc, USP | 0.45 |
| Solvent - Water | 2.46 |
| TOTAL | 6.0 |
| Top Coating | |
| Agent - HPMC, E-5 LV (Methocel) | 0.240 |
| Solvent - Water | 5.760 |
| TOTAL | 6.0 |

Those skilled in the art will understand that the Methocel solutions should be allowed to completely hydrate for at least twelve (12) hours before use.

The equipment used to prepare the sustained release dosage form according to the invention was a laboratory scale fluidized bed or air suspension coating machine (Vector Model FLM 15 with a 7 inch bottom spray from Wurster Co., Cambery, N.J.; an alternative machine would be a Model GPCG-5 from Glatt® Air Techniques Inc., Ramsey, N.J.). Air suspension coating is a widely used process by the pharmaceutical industry for the microencapsulation of drugs. It is often referred to as a Wurster machine. The process utilizes biological inert cores such as spherical sucrose pellets, also known as non-pareils USP. In this example, 3.0 kgs of 25/30 mesh non-pareils was charged to the Wurster machine to be used as the core for preparation of the dosage form. The non-pareils useful in this invention can range in diameter from 0.5 mm up to about 1.25 mm with 0.5 to about 0.6 mm being preferred.

The parameters of the machine were as follows:
Nozzle port size—1.2 mm straight flute
Partition height—30 mm to 2.5 cm
Atomization Pressure—3.0 bar
Spray mode—GPCG or FLM 15
Screen—about 60 mesh
Bottom Wurster plate—9"—B plate or GP plate The machine was warmed up with an inlet temperature setpoint of 55° C. The parameters of operation were as follows:
Inlet Temperature—40–100° C.
Product Temperature—35–55° C.
Atomization Air Pressure—2.5–4.0 bar
Spray Rate—10–100 g/min.
Air volume—100–450 cfm After the machine had properly warmed up, it was turned off and charged with 3.0 kgs of 25/30 mesh non-pareils. The machine was restarted and fluidization was begun with an inlet temperature set point of 55° C., an air volume of 120 cfm and an inlet dew point setting of 12° C. Spraying of the Therapeutic Suspension was initiated when the product temperature reached 40° C. The spray rate was started at 10 g/min. and increased by 10 g/min every 15 minutes until the spray rate reached 80 g/min. The product temperature was maintained at between 38 and 50° C. by modulation of the inlet temperature. After about 6 kg of the Therapeutic Suspension was sprayed, a sample was removed from the processing unit. The nozzle of the machine was then flushed with 100 g of water, while the phenytoin coated non-pareils were allowed to dry for 5 minutes. The enteric coating solution was then charged to the spray pump and spraying began at 2.5 bar and 20 g/min after the inlet temperature was decreased to 45° C. The spray rate was increased by 10 g/min every 15 minutes until 70 g/min was reached. Inlet temperature was modulated so as to maintain a product temperature of about 25–50° C. After the enteric coating solution was exhausted, a sample of the beads was removed from the machine. The nozzle was then flushed with 100 gms of water while curing of the enteric coating took place. The curing was accomplished through increasing the inlet temperature to 60° C. and holding it there for about 30 minutes. After the curing was completed, the inlet temperature was increased to 70° C. and the remaining portion of the Therapeutic Suspension was then sprayed at a rate of 50 g/min., while the product temperature was maintained at about 35–45° C. A sample of the beads was removed from the machine and the top coating solution was then charged to the machine. The inlet temperature was adjusted to 65° C. and spraying of the Top Coat solution was begun while the product temperature was maintained at 40–44° C. At the end of the Top Coat spraying, the batch was allowed to cool for 2 minutes with the inlet temperature set at 0° C. The beads were then discharged from the machine. The beads contained about 33 mgs of phenytoin sodium per 100 mgs of beads.

EXAMPLE II

Bioavailability Study

In this experiment, a comparative single dose, 3 way crossover, bioavailability study was conducted of the dosage form prepared in Example I (EXP) and two commercially available dosage forms of phenytoin sodium. The study used twelve (12) health adult male volunteers after signing the appropriate waivers.

The two commercially available reference products were:
1) Parke-Davis (a division of Warner-Lambert Co.) Dilantin® Kapseals®, 100 mg extended phenytoin sodium capsules, USP Lot No. 05017F, Expiration Date: December, 1998, (CON I); and
2) Parke-Davis (Dilantin®) phenytoin oral suspension 125 mg phenytoin/5 ml phenytoin suspension Lot No. 31517L, Expiration Date: December, 1998 (CON II).

The beads prepared in Example I were placed in a gelatin capsule such that 100 mg of phenytoin sodium was in each capsule (about 303–309 mgs of beads per capsule). Dosing Regimens A and B consisted of administering to the subject one capsule (100 mg of active per capsule) with 240 ml of water. Dosing Regimen C consisted of a single 5 ml (125 mg of active) dose administered with 240 ml of water.

The subjects fasted overnight prior to dosing and for at least 4 hours thereafter. Blood samples were collected from each subject prior to dosing and at 0.5, 1, 1.5, 2, 2.5, 3, 4, 5, 6, 7, 8, 12, 16, 24, 36, 48, 72 and 96 hours after dosing. Standard meals were provided at about 4 and 9 hours after dosing and at appropriate times thereafter.

The washout period between doses for the crossover was 21 days and the analyte determined was phenytoin in the plasma. The analytical method used was HPLC with U.V. detection at a limit of quantitation for phenytoin in plasma at 20 ng/ml. The pharmacokinetic parameters for plasma phenytoin were calculated as follows:

AUC 0-t: The area under the plasma concentration versus time curve, from time 0 to at the last measurable concentration, as calculated by the linear trapezoidal method.

AUCinf: The area under the plasma concentration versus time curve from time 0 to infinity. AUCinf is calculated as the sum of the AUC 0-t plus the ratio of the last measurable plasma concentration to the elimination rate constant.

AUC/AUCinf: The ratio of AUC 0-t to AUCinf.

Cmax: Maximum measured plasma concentration over the time span specified.

tmax: Time of the maximum measured plasma concentration. If the maximum value occurs at more than one time point, tmax is defined as the first time point with this value.

kel: Apparent first-order elimination or terminal rate constant calculated from a semi-log plot of the plasma concentration versus time curve. The parameter will be calculated by linear least-squares regression analysis using the last three (or more) non-zero plasma concentrations.

t½: The elimination or terminal half-life will be calculated as 0.693/kel.

No value of kel or AUCinf is reported for cases that do not exhibit a terminal log-linear phase in the concentration versus time profile. The data were dose-normalized for phenytoin.

Statistical Analysis

Statistical analyses, including the following, was performed for plasma phenytoin data. Data from all subjects that completed the study were analyzed.

Analyses of Variance

Analyses of variance was performed on the pharmacokinetic parameters listed above, with the exception of the ratio of AUC 0-t to AUCinf. Additionally, log-transformed data were used for analysis of AUC 0-t, AUCinf and Cmax. The analysis of variance model includes subjects, period, first order carryover and drug formulation as factors. A 5% level of significance was used. Each analysis of variance included a calculation of least-squares means, adjusted differences between formulation means and the standard error associated with these differences. The above statistical analyses was conducted using the SAS® GLM procedure.

Ratio Analyses

Ratios of means was calculated using the LSM for both untransformed and log-transformed AUC 0-t, AUCinf and Cmax. The geometric mean values are reported for log-transformed parameters. Ratios of means are expressed as a percentage. The comparisons of interest are EXP vs. CON I and EXP vs. CON II.

Power Tests

The power (i.e., probability of detecting a 20% difference relative to the reference formulation LSM at the 5% significance level using a t-test under the null hypothesis of zero-difference) was calculated for the untransformed and log-transformed parameters AUC 0-t, AUCinf and Cmax. Table I sets forth the results of this clinical study.

TABLE 1

Summary Of Results - Phenytoin In Plasma Pharmacokinetic Parameters (Ln = 12)

| | Ln AUC 0-t*<br>(ng -h/mL) | Ln AUCinf*<br>(ng - h/mL) | Ln Cmax*<br>(ng/ml) | tmax<br>(h) | Half-life<br>(h) | kel<br>(1/h) |
|---|---|---|---|---|---|---|
| EXP | | | | | | |
| Mean | 35681.13 | 37162.51 | 939.5382 | 7.417 | 15.97 | 0.04468 |
| CV | 26.5 | 23.9 | 22.5 | 71.5 | 17.5 | 17.9 |
| n | 12 | 12 | 12 | 12 | 12 | 12 |
| CON I | | | | | | |
| Mean | 41086.19 | 42339.18 | 1397.0244 | 2.833 | 15.73 | 0.04513 |
| CV | 23.2 | 21.9 | 17.9 | 53.4 | 16.2 | 15.9 |
| n | 12 | 12 | 12 | 12 | 12 | 12 |
| CON II | | | | | | |
| Mean | 43385.02 | 44420.25 | 1326.6918 | 4.958 | 15.08 | 0.04740 |
| CV | 20.1 | 19.4 | 18.6 | 89.0 | 18.0 | 18.6 |
| n | 12 | 12 | 12 | 12 | 12 | 12 |
| Least Square Means | | | | | | |
| EXP | 35969.66 | 37471.22 | 940.9191 | | | |
| CON I | 40656.61 | 42014.63 | 1362.5870 | | | |
| CON II | 43491.73 | 44394.60 | 1358.2259 | | | |
| Ratio of Least Squared Means | | | | | | |
| EXP/CON I % | 88.5 | 89.2 | 69.1 | | | |
| EXP/CON II % | 82.7 | 84.4 | 69.3 | | | |
| Power | | | | | | |
| EXP vs. CON I<br>(Ref. CON I) | >99.9% | >99.9% | 92.9% | | | |
| EXP vs. CON II<br>(Ref. CON II) | >99.9% | >99.9% | 92.9% | | | |
| Intrasubject CV % | 5.5 | 5.4 | 13.5 | | | |

*For Ln-transformed parameters, the antilog of the mean (i.e., the geometric mean) is reported.

Results and Discussion

Individual concentration-time profiles and pharamacokinetic parameters for plasma phenytoin are not reported herein. The results for Ln-transformed pharmacokinetic parameters AUC 0-t, AUCinf, Cmax and untransformed parameters tmax, Half-life and kel are presented in Table 1. Results for the AUC 0-t, AUCinf and Cmax parameters after adjustments for measured drug content can be found in Table 2.

EXP vs. CON I

The ratios of least-squares means for the Ln-transformed parameters AUC 0-t, AUCinf and Cmax were 88.5%, 89.2% and 69.1%, respectively. The mean tmax for the EXP delayed release capsule was 7.417 hours, compared with 2.833 hours for the CON I.

After correcting measured drug content for the Ln-transformed parameters, the ratios of least-squares means for the potency corrected Ln-transformed parameters AUC 0-t, AUCinf and Cmax are 87.8%, 88.6% and 68.6%, respectively.

EXP vs. CON II

The ratios of least-squares means for the Ln-transformed parameters AUC 0-t, AUCinf and Cmax were 82.7%, 84.4% and 69.3%, respectively. The mean tmax for the EXP delayed release capsule was 7.417 hours, compared with 4.958 hours for the CON II.

Conclusion

Based on the ratios of least-square means for Ln-transformed AUC 0-t and AUCinf, the EXP delayed release capsules in according with the invention, CON I and CON II show comparable bioavailability under fasting conditions.

TABLE 2

Potency Corrections Calculations - Adjusted Ratios of Means Pharmacokinetic Parameters
Ln AUC 0-t Ln AUCinf and Ln Cmax

| | Ln AUC 0-t<br>(ng - h/mL) | Ln AUCinf<br>(ng-h./mL) | Ln Cmax<br>(ng/mL) |
|---|---|---|---|
| Ratio of Least-Squares Means (EXP/CON I %) | 87.8 | 88.6 | 68.6 |
| Ratio of Least-Squares Means (EXP/CON II %) | TBD | TBD | TBD |

TABLE 3

| | Active - % of Label Claim |
|---|---|
| Formulation | Measured Content (% of label claim) |
| EXP | 98.3% |
| CON I | 97.6% |
| CON II | TBD |

EXAMPLE III

Preparation of 48/52 Beads According to the Invention

Using a therapeutic suspension, enteric coating and top coating, as described in Example 1, a second batch of phenytoin sodium in the dosage form according to the invention was prepared. The major difference was that about 48% by weight of the active was interior to the enteric coating and about 52% was outside the enteric coating.

Equipment set up and operation thereof was similar to that set forth in Example I except that delivery levels for the first and second coats of therapeutic suspension were adjusted to accomplish the 48/52 split of active. The final product beads contained about 33 mgs of phenytoin sodium per 100 mgs of beads. The beads were uniform in size, free flowing, stable to atmospheric conditions and pearl white in color.

EXAMPLE IV

Bioavailability Study

The study set forth in Example II was repeated except that six (6) subjects were evaluated over a 24 hour period. The results (unavailable at the time of filing this application) will evidence that the 48/52 formulation will have a shorter Tmax, greater Cmax and larger AUC than the formulation prepared in Example I.

EXAMPLE V

Preparation of Beads According to the Invention with an Edible Acid in the Enteric Coating The procedure and ingredients set forth in Example I are used in this Example, except that the Enteric Coating solution additionally contains 2 kg of fumaric acid, for a total of 8.0 kg of Enteric Coating solution. The Therapeutic Suspension, the Enteric Coating and the Top Coating solution are utilized as described in Example I.

EXAMPLE VI

Preparation of Beads According to the Invention Without a Protective Coating

The procedure and ingredients set forth in Example I are used in this Example, except that application of the Top Coat solution is omitted. The finished beads contain about 34 mgs of phenytoin sodium per 100 mgs of beads.

EXAMPLE VII

Preparation of Beads According to the Invention with Two layers of Enteric Coating The compositions set forth in Example I are used, except that a Second Enteric coating is prepared.

| SECOND ENTERIC COATING | |
|---|---|
| INGREDIENT | AMOUNT Kg |
| Polymer - Eudragit S-100 | 3.0 |
| Plasticizer - Triethyl citrate | 0.09 |
| Anti-Tack - Talc, USP | 0.45 |
| Solvent - 60/40 ratio of ethyl alcohol/water | 2.46 |

The equipment set forth in Example I is used, however, the procedure is modified to place the second enteric coating over the core of the therapeutic agent. The Therapeutic Suspension is divided to result in 25% by weight in the core, 50% by weight in the second layer and 25% by weight in the third layer. The beads contain about 25.5 mgs of phenytoin per 100 mgs of beads.

Industrial Applicability

While many drugs are conveniently dosed using conventional delayed release or sustained release technology, certain pharmaceuticals whose solubility is highly dependent upon pH present special problems. Pharmaceuticals such as phenytoin sodium which have extended half-lives and whose therapeutically effective plasma concentrations are rather narrow present especially difficult problems. The present inventors have, through an extensive amount of research, determined that a core of therapeutic agent surrounded by an enteric coating which is then surrounded by additional active ingredient, can be effectively manipulated to utilize the drug's variable pH solubility to the patient's benefit. It is the application of this technology to a certain class of pharmaceuticals that represents a substantial advancement in the state of the art.

Having thus described the present invention in detail, it will be obvious to those skilled in the art that various changes or modifications may be made without departing from the scope of the invention defined in the appended claims and described in the specification.

We claim:

1. An oral dosage delivery form adapted to deliver a pH dependent water soluble therapeutic agent comprising:
    (a) a core comprising said therapeutic agent in an amount sufficient to deliver a first portion of an effective amount of said therapeutic agent over the intended delivery time;
    (b) an enteric polymer coating over said core wherein said coating comprises an edible acid at a weight percent concentration of from 10 to 80%; and
    (c) a coating of said therapeutic agent over said enteric polymer coating in an amount sufficient to deliver a second portion of an effective amount of said therapeutic agent over the intended delivery time.

2. The oral dosage delivery form according to claim 1 wherein said first portion is 25 to 75% of an effective amount of said therapeutic agent.

3. The oral dosage delivery form according to claim 1 wherein said second portion is 25 to 75% of an effective amount of said therapeutic agent.

4. The oral dosage delivery form according to claim 1 wherein said form additionally comprises a protective coating over said second portion of therapeutic agent.

5. The oral dosage delivery form according to claim 1 wherein said therapeutic agent is selected from the group consisting of phenytoin sodium, diphenhydramine hydrochloride, dimenhydrinate, bromodiphenhydramine hydrochloride, doxylamine succinate, phenyltoloxamine dihydrogen citrate, carbinoxyamine maleate, methaphenilene hydrochloride, chlorpheniramine maleate, promethazine hydrochloride, cyclizine hydrochloride, diltiazam hydrochloride, disopyramide phosphate, iodohippurate sodium, phenylpropanolamine hydrochloride, propranolol hydrochloride, thiopental sodium, mephenesin carbamate, hydroxyzine hydrochloride, benactyzine hydrochloride, methamphetamine hydrochloride, phenylpropanol-amine hydrochloride, ephedrine sulfate, phendimetrazine bitartrate and iproniazid phosphate.

6. The oral dosage form according to claim 1 wherein said core additionally comprises at least one component selected from the group consisting of adhesives, anti-tack agents, disintegrants, antifoam agents, lubricants and sodium lauryl sulfate.

7. The oral dosage form according to claim 1 wherein said enteric polymer coating additionally comprises at least one component selected from the group consisting of plasticizers, edible acids, and anti-tack agents.

8. The oral dosage form according to claim 1 wherein said enteric polymer is selected from the group consisting of ethylcellulose, hydroxypropylcellulose, carboxymethylcellulose, acrylic resins, shellac, wax, ethylacrylate methacrylic acid copolymers and mixtures thereof.

9. The oral dosage form according to claim 8 wherein said ethylacrylate methacrylic acid copolymer has a molecular weight of about 250,000.

10. The oral dosage form according to claim 2 wherein said first portion is 45–55% of said effective amount.

11. The oral dosage form according to claim 10 wherein said first portion is 48–52% of said effective amount.

12. The oral dosage form according to claim 1 wherein said therapeutic agent is phenytoin sodium and said phenytoin sodium is in admixture with sodium lauryl sulfate.

13. An oral dosage delivery form comprising:
(a) a core comprising phenytoin sodium, sodium lauryl sulfate and a disintegrant, said core containing 25–75% by weight of an effective amount of said phenytoin sodium over the intended delivery time;
(b) an enteric coating over said core, said enteric coating comprising an ethylacrylate methacrylic acid copolymer, an edible acid, and a plasticizer; and
(c) a coating over said enteric coating comprising phenytoin sodium, sodium lauryl sulfate and a disintegrant, said coating containing 25–75% by weight of an effective amount of said phenytoin sodium over the intended delivery time.

14. A method for the preparation of a sustained release pharmaceutical dosage form comprising the steps of:
(a) preparing an aqueous suspension of a therapeutic agent wherein said agent's solubility is pH dependent;
(b) preparing an enteric coating aqueous solution comprising a material that does not dissolve or disperse in gastric juices and an edible acid;
(c) charging an air suspension coating machine with biologically inert spherical pellets;
(d) spraying 25–75 weight % of said suspension of therapeutic agent while said air suspension coating machine is in operation to coat said inert pellets; thereafter
(e) spraying said enteric coating aqueous solution to coat the pellets of step (d); and thereafter
(f) spraying the remainder of said suspension of therapeutic agent to coat the pellets of step (e).

15. The method according to claim 14 wherein said therapeutic agent is selected from phenytoin sodium, diphenhydramine hydrochloride, dimenhydrinate, bromodiphenhydramine hydrochloride, doxylamine succinate, phenyltoloxamine dihydrogen citrate, carbinoxyamine maleate, methaphenilene hydrochloride, chlorpheniramine maleate, promethazine hydrochloride, cyclizine hydrochloride, diltiazan hydrochloride, disopyramide phosphate, iodohippurate sodium, phenylpropanolamine hydrochloride, propranolol hydrochloride, thiopental sodium, mephenesin carbamate, hydroxyzine hydrochloride, benactyzinc hydrochloride, methamphetamille hydrochloride, phenylpropanol-amine hydrochloride, ephedrine sulfate, phendimetrazine bitartate and iproniazid phosphate.

16. The method according to claim 14 wherein said enteric coating aqueous solution comprises an ethylacrylate methacrylic acid copolymer and fumaric acid.

17. The method according to claim 14 wherein said aqueous suspension comprises phenytoin sodium, a disintergrant and sodium lauryl sulfate.

18. The method according to claim 16 wherein said copolymer has a molecular weight of 250,000.

19. The method according to claim 14 wherein 45–55 weight % of said suspension is sprayed in step (d).

20. The oral dosage delivery form according to claim 13 wherein said edible acid is selected from the group consisting of acetic acid, benzoic acid, fumaric acid, sorbic acid, propionic acid, hydrochloric acid, citric acid, malic acid, tartaric acid, isocitric acid, oxalic acid, lactic acid, the phosphoric acids and mixtures thereof.

21. The method according to claim 14 wherein said edible acid is selected from the group consisting of acetic acid, benzoic acid, fumaric acid, sorbic acid, propionic acid, hydrochloric acid, citric acid, malic acid, tartaric acid, isocitric acid, oxalic acid, lactic acid, the phosphoric acids, and mixtures thereof.

22. An oral dosage delivery form adapted to deliver a pH dependent water soluble therapeutic agent comprising:
a) a core comprising said therapeutic agent in an amount sufficient to deliver a first portion of an effective amount of said therapeutic agent over the intended delivery time;
b) a first enteric polymer coating over said core;
c) a second layer of said therapeutic agent in an amount sufficient to deliver a second portion of an effective amount of said therapeutic agent over the intended delivery time;
d) a second enteric polymer coating over said second layer of therapeutic agent; and
e) a third layer of said therapeutic agent over said second enteric polymer coating in an amount sufficient to deliver a third portion of an effective amount of said therapeutic agent over the intended delivery time.

23. The oral dosage delivery form according to claim 22 wherein said first, second and third portions of said therapeutic agent can independently range from 25 to 75% of an effective amount of said therapeutic agent over the intended delivery time.

24. The oral dosage delivery form according to claim 22 wherein said form additionally comprises a protective coating over said third layer of therapeutic agent.

25. The oral dosage delivery form according to claim 22 wherein said core is formed around a non-pareil.

26. The oral dosage delivery form according to claim 22 wherein said core additional comprises adhesives, anti-tack agents, disintegrants, antiforming agents and lubricants.

27. The oral dosage delivery form according to claim 22 wherein said core comprises phenytoin sodium and sodium laltryl sulfate.

28. The oral dosage delivery form according to claim 22 wherein said enteric polymer coating additionally comprises plasticizers and anti-tack agents.

29. The oral dosage delivery form according to claim 22 wherein said therapeutic agent is selected from the group consisting, of phenytoin sodium, diphenhydramine hydrochloride, dimenhydrinate, bromodiplhenhydramine hydrochloride, doxylamine succinate, phenyltoloxamine dihydrogen citrate, carbinoxyamine maleate, methaphenilene hydrochloride, chlorpheniramine maleate, promethazine hydrochloride, cyclizine hydrochloride, diltiazan hydrochloride, disopyramide phosphate, iodohippurate sodium, phenylpropanolamine hydrochloride, propranolol hydrochloride, thiopental sodium, mephenesin carbamate, hydroxyzine hydrochloride, benactyzine hydrochloride, methamphetamine hydrochloride, phenylpropanol-amine hydrochloride, ephedrine sulfate, phendimietrazine bitartate and iproniazid phosphate.

30. The oral dosage delivery form according to claim 22 wherein said enteric polymer coating additionally comprises at least one component selected from the group consisting of plasticizers, edible acids and anti-tack agents.

31. The oral dosage delivery form according to claim 22 wherein said enteric polymer is selected from the group consisting of ethylcellulose, hydroxypropylcellulose, carboxymethylcellulose, acrylic resins, shellac, wax, ethylacrylate methacrylic acid copolymers and mixtures thereof.

32. The oral dosage delivery form according to claim 31 wherein said etlylacrylate methacrylic acid copolymer has a molecular weight of about 250,000.

* * * * *